(12) United States Patent
Takashima et al.

(10) Patent No.: US 6,780,633 B2
(45) Date of Patent: Aug. 24, 2004

(54) METHODS FOR PRODUCING OPTICALLY ACTIVE AMINO ACIDS

(75) Inventors: Yoshiki Takashima, Nishinomiya (JP); Eiji Nitta, Nishinomiya (JP); Yuko Kobayashi, Toyonaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/537,416

(22) Filed: Mar. 29, 2000

(65) Prior Publication Data

US 2002/0173009 A1 Nov. 21, 2002

(30) Foreign Application Priority Data

Apr. 5, 1999 (JP) ............................ 11-097570

(51) Int. Cl.$^7$ ................................ C12P 13/04
(52) U.S. Cl. ..................... 435/280; 435/106; 435/128; 435/136
(58) Field of Search ................ 435/280, 128, 435/136, 106

(56) References Cited

U.S. PATENT DOCUMENTS

| | | | | |
|---|---|---|---|---|
| 4,510,246 A | * | 4/1985 | Wolfe et al. ................ | 435/183 |
| 5,316,943 A | | 5/1994 | Kidman et al. | |
| 6,204,050 B1 | * | 3/2001 | Dicosimo et al. ........... | 435/280 |

FOREIGN PATENT DOCUMENTS

| | | |
|---|---|---|
| EP | 0 135 846 A2 | 4/1985 |
| EP | 0 310 846 A2 | 4/1989 |
| WO | WO 91/05870 | 5/1991 |

OTHER PUBLICATIONS

Kim et al., "A New Amino Acid Racemase with Threonine alpha epimerase Activity from *Pseudomonas putida*: Purification and Characterization" J. Bacteriology 175 (13) : 4213–17 (1993).*

ATCC Catalog of Bacteria and Bacteriophages, 19th edition, p. 168 (1996).*

Gosling et al. "Purification and Characterization of D Amino–Acid Amino Transferase from Rhizobium–Japonicum", Biochem. Biophys. Acta 522 (1) : 84–95 (1978).*

Hashimoto et al., "L–Alanine Fermentation by an Alanine Racemase–Deficient Mutant of the DL–Alanine Hyperproducing Bacterium Arthrobacter Oxydans HAP–1", J. Ferment. Bioengineer. 86 (4) : 385–390 (1998).*

Ian G. Fotheringham et al., "Aminotransferase–Catalyzed Conversion of D–Amino Acids to L–Amino Acids", *Biotechnol. Prog.*, vol. 7, 1991, pp. 380–381.

Leonila Làiz et al., "Purification and characterization of the isopenicillin N epimerase from *Nocardia lactamdurans*", *Journal of General Microbiology*, vol. 136, 1990, pp. 663–371.

Taylor, P. P. et al.: "Novel biosynthetic approaches to the production of unnatural amino acids using transaminases", Trends in Biotechnology, GB, Elsevier Publication, Cambridge, vol. 16, No. 10, Oct. 1, 1998, pp. 412–418, XP004145648, ISSN: 0167–7799.

* cited by examiner

*Primary Examiner*—Irene Marx
(74) *Attorney, Agent, or Firm*—Sughrue Mion, PLLC

(57) ABSTRACT

A method for producing from one of the optical isomers (optical isomer I) of an amino acid represented by Formula (1):R—CH(NH$_2$)—COOH (1), wherein R is defined in the specification, the other of the optical isomers (optical isomer II), said method comprising reacting a biological material which has an ability of converting said one of the optical isomers (optical isomer I) to said the other of the optical isomers (optical isomer II), the isomerism being on the basis of an assymetric carbon atom to which both of an amino group and a carboxyl group are bound and said ability being not inhibited seriously by an amino acid transferase inhibitor β-chloro-D-alanine, β-chloro-L-alanine or gabaculine, with said one of the optical isomers (optical isomer I).

11 Claims, No Drawings

METHODS FOR PRODUCING OPTICALLY ACTIVE AMINO ACIDS

BACKGROUND OF THE INVENTION

1. Field of the Invention

The present invention relates to a method for producing an optically active amino acid and the like.

2. Description of the Prior Art

An optically active amino acid is known to be a compound which is useful as an intermediate for a pharmaceutical such as an anti-asthmatic agent, an anti-depressant and an anti-thrombotic agent and as a feed or food additive and the like.

A biochemical method for producing an optically active amino acid is believed generally to be advantageous in terms of the simplicity of an operation, the yield of a product, the prices of starting materials and the optical purity of an intended substance when compared with a synthetic chemical method. Such biochemical method may for example be a method in which one of the optical isomers of an amino acid as a racemic mixture is decomposed, a method in which an aminoacyl-form of an amino acid as a racemic mixture is deacylated in an optically selective manner, a method in which an amino acid as a L-form is produced from a keto acid in the presence of an amino-donating compound and a method utilizing a fermentation of a microorganism.

SUMMARY OF THE INVENTION

An objective of the present invention is to provide a method for producing an optically active amino acid effeciently.

Now we discovered a biological material which has an ability of converting one of the optical isomers of a certain amino acid to the other of the optical isomers, the isomerism being on the basis of an asymmetric carbon atom to which both of an amino group and a carboxyl group are bound and the ability described above being not inhibited seriously by an aminotransferase inhibitor-chloro-D-alanine, -chloro-L-alanine or gabaculine, and finally established the present invention by applying said biological material to the production of an optically active amino acid of the amino acid described above.

That is, the present invention provides:

1. A method for producing from one of the optical isomers (optical isomer I) of an amino acid represented by Formula (1):

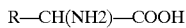
    R—CH(NH2)—COOH    (1)

(wherein R is an optionally substituted C1–C12 alkyl group, an optionally substituted C4–C8 cycloalkyl group or an optionally substituted C6–C14 aryl group) (hereinafter, it is sometimes referred to as the amino acid (1)) the other of the optical isomers (optical isomer II), said method comprising reacting a biological material which has an ability of converting said one of the optical isomers (optical isomer I) to said the other of the optical isomers (optical isomer II), the isomerism being on the basis of an asymmetric carbon atom to which both of an amino group and a carboxyl group are bound and said ability being not inhibited seriously by an aminotransferase inhibitor -chloro-D-alanine, -chloro-L-alanine or gabaculine, with said one of the optical isomers (optical isomer I). (Hereinafter, it is sometimes referred to as the method of the present invention.)

2. the method according to the above 1, wherein said one of the optical isomers (optical isomer I) is a D-form and said the other of the optical isomers (optical isomer II) is a L-form.

3. the method according to the above 1, wherein said one of the optical isomers (optical isomer I) with which said biological material is reacted is present in a mixture of said the other of the optical isomers (optical isomer II).

4. the method according to the above 1, wherein said biological material is a whole cell.

5. the method according to the above 1, wherein said biological material is one derived from a microorganism belonging to the genus Arthrobacter, Flavimonas, Klebsiella, Nocardia, Pseudomonas, Rhizobium, Saccharopolyspora or Streptomyces.

6. the method according to the above 1, wherein said biological material is one derived from a microorganism classified to *Arthrobacter pascens, Flavimonas oryzihabitans, Klebsiella planticola, Nocardia diaphanozonaria, Pseudomonas chlororaphis, Pseudomonas oleovorans, Pseudomonas oxalaticus, Pseudomonas taetrolens, Rhizobium meliloti, Saccharopolyspora hirsuta or Streptomyces roseus.*

7. the method according to the above 1, wherein said biological material is one derived from *Arthrobacter pascens* strain IFO12139, *Flavimonas oryzihabitans* strain JCM2952, *Klebsiella planticola* strain JCM7251, *Nocardia diaphanozonaria* strain JCM3208, *Pseudomonas chlororaphis* strain IFO3521, *Pseudomonas oleovorans* strain IFO13583, *Pseudomonas oxalaticus* strain IFO13593, *Pseudomonas taetrolens* strain IFO3460, *Rhizobium meliloti* strain IFO14782, *Saccharopolyspora hirsuta* subsp.kobensis strain JCM9109 or *Streptomyces roseus* strain IFO12818.

8. a method for improving the optical purity of an amino acid represented by Formula (1):

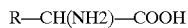
    R—CH(NH2)—COOH    (1)

(wherein R is an optionally substituted C1–C12 alkyl group, an optionally substituted C4–C8 cycloalkyl group or an optionally substituted C6–C14 aryl group), said method comprising reacting a biological material which has an ability of converting one of the optical isomers (optical isomer I) of said amino acid to the other of the optical isomers (optical isomer II), the isomerism being on the basis of an asymmetric carbon atom to which both of an amino group and a carboxyl group are bound and said ability being not inhibited seriously by an aminotransferase inhibitor β-chloro-D-alanine, β-chloro-L-alanine or gabaculine, with said amino acid represented by Formula (1).

9. the method according to the above 8, wherein said one of the optical isomers (optical isomer I) is a D-form and said the other of the optical isomers (optical isomer II) is a L-form.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

The invention is described in detail below.

A biological material which can be employed in the present invention is a biological material which has an ability of converting one of the optical isomers (optical isomer I) of the amino acid (1) to the other of the optical isomers (optical isomer II), the isomerism being on the basis of an asymmetric carbon atom to which both of an amino group and a carboxyl group are bound and the ability being not inhibited seriously by an aminotransferase inhibitor β-chloro-D-alanine, β-chloro-L-alanine or gabaculine (hereinafter sometimes referred to as the biological material of the present invention).

The ability being not inhibited seriously by an aminotransferase inhibitor β-chloro-D-alanine, β-chloro-L-alanine or gabaculine described herein means that the converting ability in the presence of an inhibitor is about 70% or more of thrat in the absence of the inhibitor when assuming the ability in the absence of the inhibitor to be 100%. Furthermore, it is preferred to be the ability being not inhibited substantially by an aminotransferase inhibitor β-chloro-D-alanine, β-chloro-L-alanine or gabaculine described herein means that the converting ability in the presence of an inhibitor is about 90% or more of that in the absence of the inhibitor when assuming the ability in the absence of the inhibitor to be 100%.

While a conversion reaction described above involves the formation of a product (optical isomer II) corresponding to the consumption of a substrate (optical isomer I) until an equilibrium is established and consequently the reaction rate is reduced as time elapses, the product linearly increases with time at an early stage of the reaction where the substrate is present in a large excess, resulting in a reaction rate specific to the relevant condition. Accordingly, an experimental value observed at an early stage of the reaction is used suitably for evaluating the converting ability described above, but a value observed at the stage of the equilibrium may also be used because of the fact that, at an early stage of the reaction, a certain combination of the type or the quantity of a substrate or the form or the quantity of the biological material of the present invention may pose a difficulty in stabilizing the reaction or the observed value is fluctuated due to a less consumption of the substrate or a less formation of the product. It is a matter of course that the values at both stages may together be taken into account to make a comprehensive decision.

β-chloroalanine is known to be an inhibitor of aspartate aminotransferase (E.C. 2.6.1.1) and D-alanine aminotransferase (E.C. 2.6.1.21) and gabaculine is known to be an inhibitor of D-alanine aminotransferase (E.C. 2.6.1.21), β-alanine-pyruvate aminotransferase (E.C. 2.6.1.18) and 4-aminobutyrate aminotransferase (E.C.2.6.1.19).

The biological material of the present invention may be employed in various forms such as a microorganism culture and a microorganism cell separated from a microorganism culture by a centrifugation as well as those obtained therefrom by certain treatments. Those obtained by certain treatments referred herein may for example be lyophilized cells, acetone-dried cells, ground cells, autolyzed cells, ultrasonicated cells, alkali-treated cells, organic solvent-treated cells, cell free extract, crude enzymes, a purified enzyme and the like, as well as an immobilized material obtained therefrom by making any of the materials listed above immobilized in accordance with a known method such as a carrier support method employing an adsorption onto an inorganic carrier such as a silica gel or a ceramic material, a polysaccharide derivative such as a DEAE-cellulose, a synthesized polymer such as Amberite IRA-935 (manufactured by Rohm and Haas) and an inclusion method employing an inclusion into a network matrix of a polymer such as a polyacrylamide, a sulfur-containing polysaccharide gel (e.g. carrageenan gel), an alginic acid gel, an agar gel and the like.

A preferred example of the biological material of the present invention may be a material derived from a microorganism belonging to the genus Arthrobacter, Flavimonas, Klebsiella, Nocardia, Pseudomonas, Rhizobium, Saccharopolyspora and Streptomyces, preferably a material derived from a microorganism classified to *Arthrobacter pascens, Flavimonas oryzihabitans, Klebsiella planticola, Nocardia diaphanozonaria, Pseudomonas chlororaphis, Pseudomonas oleovorans, Pseudomonas oxalaticus, Pseudomonas taetrolens, Rhizobium meliloti, Saccharopolyspora hirsuta* and *Streptomyces roseus*, and typically a material derived, from *Arthrobacter pascens* strain IFO12139, *Flavimonas oryzihabitans* strain JCM2952, *Klebsielia planticola* strain JCM7251, *Nocardia diaphanozonaria* strain JCM3208, *Pseudomonas chlororaphis* strain IFO3521, *Pseudomonas oleovorans* strain IFO13583, *Pseudomonas oxalaticus* strain IFO13593, *Pseudomonas taetrolens* Strain IFO3460, *Rhizobium meliloti* strain IFO14782, *Saccharopolyspora hirsuta* subsp.*kobensis* strain JCM9109 and *Streptomyces roseus* strain IFO12818.

When the biological material of the present invention is a microorganism, it may be a wild strain of a microorganism or a variant derived from such wild strain by means of a treatment with a reagent or UV, provided that it possesses the ability described above.

Such microorganism (hereinafter sometimes referred to as the microorganism of the present invention) may be prepared by the following cultivation.

The composition of the medium for cultivating the microorganism of the present invention is not particularly limited, and a medium employed usually for culturing a microorganism which contains a carbon source and a nitrogen source, organic and inorganic salts as appropriate may be employed. A carbon source may for example be a saccharide such as glucose, fructose, sucrose, dextrin and the like, a sugar alcohol such as glycerol, sorbitol and the like, an organic acid such as fumaric acid, citric acid, pyruvic acid and the like. The amount of a carbon source listed above to be added to a medium is usually about 0.1% (w/v) to about 10% (w/v). A nitrogen source may for example be an ammonium salt of an inorganic acid such as ammonium chloride, ammonium sulfate, ammonium phosphate and the like, an ammonium salt of an organic acid such as ammonium fumarate, ammonium citrate and the like, a natural organic nitrogen source such as meat extract, yeast extract, malt extract, soybean powder, corn steep liquor, cottonseed oil, dried yeast, casein hydrolysate and the like, as well as amino acids. Among those listed above, natural organic nitrogen sources and amino acids may mostly be employed also as carbon and nitrogen sources. The amount of a nitrogen source to be added is usually about 0.1% (w/v) to about 10% (w/v). An inorganic salt may for example be a phosphate such as potassium phosphate, dipotassium phosphate, sodium phosphate, disodium phosphate and the like, a chloride such as potassium chloride, sodium chloride, cobalt chloride hexahydrate and the like, a sulfate such as magnesium sulfate, ferrous sulfate heptahydrate, zinc sulfate heptahydrate, manganese sulfate trihydrate and the like, and the amount to be added is usually about 0.0001% (w/v) to about 1% (w/v).

The microorganism of the present invention may be cultivated in accordance with a conventional method employed to culture a microorganism, including a solid phase cultivation, a liquid phase cultivation (a tube shaking cultivation, a reciprocal shaking cultivation, a rotary shaking cultivation, a jar fermentation Oar fermenter cultivation, a tank cultivation) and the like. Especially when a jar fermenter is employed, an aseptic air should be introduced into the jar fermenter usually at an aeration rate of about 0.1 to about 2 times the culture fluid volume per minute. The temperature at which the cultivation is performed may vary within the range allowing a microorganism to be grown, and it is preferred to perform the cultivation, for example, at a temperature ranging from about 15° C. to about 40° C. and at a pH of the medium ranging from about 6 to about 8. The cultivation time may vary depending on the various factors of the cultivation conditions, and a time ranging from about 1 day to about 10 days is usually preferred.

The microorganism of the present invention may for example be selected based on the ability of converting p-chlorophenylalanine as a racemic mixture into an optically active p-chlorophenylalanine. Correspondingly to the stereochemistry of the resultant optical isomer obtained as descried above, the selected microorganism may be used in the production of one of the optical isomers, L or D-form, of the amino acid (1) as intended.

R of the amino acid (1) of the invention is an optionally substituted C1–C12 alkyl group (a C1–C12 alkyl group, a substituted C1–C12 alkyl group), an optionally substituted C4–C8 cycloalkyl group (a C4–C8 cycloalkyl group, a substituted C4–C8 cycloalkyl group), an optionally substituted C6–C14 aryl group (a C6–C14 aryl group or a substituted C6–C14 aryl group). The C1–C12 alkyl group may for example be methyl, ethyl, propyl, 1-methylethyl, 2-methylpropyl, 1-methylpropyl, 1,1-dimethylethyl, penthyl, hexyl, heptyl, octyl, nonyl, decyl, undecyl, dodecyl groups and the like, and the C4–C8 cycloalkyl group may for example be cyclobutyl, cyclopentyl, cyclohexyl, cycloheptyl, cyclooctyl groups and the like, and the C6–C14 aryl group may for example be phenyl and naphthyl groups.

The term "substituted" used herein with respect to the substituted C1–C12 alkyl group as R means that one or more, usually 1 to 5 hydrogen atoms in the alkyl group are substituted with same or different substituents selected from the group consisting of a C4–C8 cycloalkyl group; a C4–C8 cycloalkyl group substituted by one or more groups selected from the group consisting of a C1–C3 alkyl group, a C1–C3 alkoxy group, an amino group, a cyano group, a hydroxyl group and a halogen atom; a C1–C2 alkoxy group; a C1–C2 alkylthio group; a methylenedioxy group; a hydroxyl group; a cyano group; a carboxyl group; a C2–C5 alkyloxycarbonyl group; an amino group; a mono- or di(C1–C5)alkylamino group; an aminocarbonyl group; a guanidino group; a 3-indolyl group; a mercapto group; a phenyl group; a phenyl group substituted by one or more groups selected from the group consisting of a C1–C3 alkyl group, a C1–C3 alkoxy group, an amino group, a cyano group, a benzyloxy group, a hydroxyl group and a halogen atom; a phenoxy group; a phenoxy group substituted by one or more groups selected from the group consisting of a C1–C3 alkyl group, a C1–C3 alkoxyl group, an amino group, a cyano group, a benzyloxy group, a hydroxyl group and a halogen atom; a napthyl group; a naphthyl group substituted by one or more groups selected from the group consisting of a C1–C3 alkyl group, a C1–C3 alkoxy group, an amino group, a cyano group, a benzyloxy group, a hydroxyl group and a halogen atom; a benzyloxy group and a halogen atom. Preferred substituents may for example be methyl, ethyl, cyclohexyl, methoxy, ethoxy, methylthio, ethylthio, aminocarbonyl, guanidino, 3-indolyl, mercapto, methylenedioxy, hydroxyl, cyano, amino, carboxyl, phenyl, benzyloxy, dibenzyloxyphenyl and methylenedioxyphenyl groups, as well as fluorine, chlorine and bromine atoms.

The term "substituted" used herein with respect to the substituted C4–C8 cycloalkyl group as R means that one or more, usually 1 to 3 hydrogen atoms in the cycloalkyl group are substituted with same or different substituents selected from the group consisting of a C1–C3 alkyl group, C1–C3 alkoxy group, an amino group, a cyano group, a hydroxyl group and a halogen group.

The term "substituted" used herein with respect to the substituted C6–C14 aryl group as R means that one or more, usually 1 to 5 hydrogen atoms in the aryl group are substituted with same or different substituents selected from the group consisting of a C1–C3 alkyl group; a C1–C2 halogenated alkyl group; a C1–C2 alkoxy group; a methylenedioxy group; a hydroxyl group; a cyano group; a carboxyl group; a C2–C5 alkyloxycarbonyl group; an amino group; a mono- or di(C1–C5)alkylamino group; a phenyl group; a phenyl group substituted with one or more substituents selected from a C1–C3 alkyl group, a C1–C3 alkoxy group and a hydroxyl group; a phenoxy group; a phenoxy group substituted with one or more substituents selected from a C1–C3 alkoxy group and a hydroxyl group; a benzyloxy group; and a halogen atom, and preferably with same or different substituents selected from the group consisting of methyl, ethyl, monochloromethyl, trifluoromethyl, methoxy, methylenedioxy, hydroxyl, cyano, amino, carboxyl, phenyl and benzyloxy groups as well as fluorine, chlorine and bromine atoms.

Typically as a preferred R, the C1–C12 alkyl group or the substituted C1–C12 alkyl group may for example be methyl, ethyl, propyl, butyl, 1-methylethyl, 2-methylpropyl, 1-methylpropyl, 1,1-dimethylethyl, 3-guanidinopropyl, 3-indolylmethyl, hydroxymethyl, 1-hydroxyethyl, 2-hydroxyethyl, methylthioethyl, ethylthioethyl, 4-aminobutyl, carboxymethyl, carboxyethyl, aminocarbonylmethyl, aminocarbonylethyl, benzyl, p-hydroxyphenylmethyl, p-chlorophenylmethyl, p-fluorophenylmethyl, m-cyanophenylmethyl and naphthylmethyl groups.

The C4–C8 cycloalkyl group or the substituted C4–C8 cycloalkyl group may for example be cyclohexyl and 4-chlorocyclohexyl groups, and a C6–C14 aryl group or a substituted C6–C14 aryl group may for example be phenyl, p-hydroxyphenyl, p-chlorophenyl and naphthyl groups.

The amino acid (1) of the present invention may for example be alanine, norvaline, tert-leucine, methionine, 2-aminobutyric acid, 2-aminoadipic acid, serine, O-methylserine, threonine, phenylglycine, phenylalanine, p-chlorophenylalanine, p-fluorophenylalanine, naphthylglycine, naphthylalanine and the like.

In the method of the present invention, when the other of the optical isomers (optical isomer II), i.e., the amino acid (1) as intended, is an L-form, then the biological material of the present invention employed is one having an ability of converting a D-form of the amino acid (1) to the L-form thereof and a starting material employed may be only that one of the optical isomers (optical isomer I), i.e., the D-form of the amino acid (1) or may be a mixture of the D-form and the L-form. When the other of the optical isomers (optical isomer II), i.e., the amino acid (1) as intended, is a D-form, then the biological material of the present invention employed is one having an ability of converting an L-form of the amino acid (1) to the D-form thereof and a starting material employed may be only that one of the optical isomers (optical isomer I), i.e., the L-form of the amino acid (1) or may be a mixture of the D-form and the L-form. When such mixture of the D-form and the L-form of the amino acid (1) is employed, the ratio between them is not particularly limited, and it is preferred industrially to employ an about 1:1 racemic mixture. Alternatively, a mixture in which an intended isomer is contained at a relatively high ratio is produced preliminary by any method, and then the mixture is subjected to the method of the present invention.

The method of the present invention is performed usually in an aqueous buffer solution containing a salt of an inorganic acid such as a salt of an alkaline metal phosphate such as sodium phosphate and potassium phosphate and a salt of an organic acid such as a salt of an alkaline metal acetate such as sodium acetate and potassium acetate, and the concentrations of the amino acid (1) in a reaction mixture of the method of the present invention is usually 30% (w/v) or lower, preferably 0.01 to 20% (w/v). The amount of the biological material of the present invention may be selected based on various factors such as the reaction time or the selectivity for an L- or D-form of the amino acid (1) to be yielded. For example, the amount is usually 0.01 to 200 parts by weight, preferably 0.1 to 50 parts by weight based on the amino acid (1). The reaction temperature is usually 10 to 70° C., preferably 20 to 60° C. The pH of the reaction mixture is usually 4 to 12, preferably 5 to 11. The reaction time period may be selected appropriately based on a desirable isomer ratio and the like. Usually, the reaction time is 16 to 120 hours, and the completion of the reaction may be ensured by any monitoring method such as HPLC.

A reaction mixture may further contain an auxiliary agent such as a surfactant, a coenzyme, a metal salt, a trace nutrition or an organic solvent in order to reduce the reaction time and to increase the conversion rate, and such auxiliary agents may be added to a reaction mixture alone or in combination with each other as appropriate. A surfactant to be used may for example be sodium dodecylsulfate, polyethylene glycol mono-p-isooctylphenylether, cetylpyridinium bromide and the like, and a coenzyme may for example be nicotinamideadenine dinucleotide, nicotinamideadenine dinucleotide phosphate, adenosine-5'-phosphate, flavine mononucleotide, pyridoxal phosphate and coenzyme A and the like. A metal salt may for example be monopotassium dihydrogen phosphate, disodium monohydrogen phosphate, magnesium sulfate heptahydrate, ferrous sulfate heptahydrate, zinc sulfate heptahydrate, manganese sulfate trihydrate, cobalt chloride hexahydrate and the like, and a trace nutrition may for example be a yeast extract. An organic solvent may for example be an alkane such as n-heptane, cyclohexane and isooctane, an ether such as methyl-tert-butylether, an alcohol such as methanol, isopropanol and n-octanol, a sulfoxide such as DMSO, a ketone such as acetone, a keto acid such as oxaloacetic acid, pyruvic acid and α-ketobutyric acid, an alkaline metal salt of a keto acid such as sodium pyruvate, an alkylester of a keto acid such as methyl pyruvate.

The other of the optical isomers (optical isomer II), i.e., an L- or D-form of the amino acid (1) thus produced may be recovered from a reaction mixture by a known method. For example, the biological material of the present invention is separated from a reaction mixture by a centrifugation or an equivalent method to obtain a supernatant, which are then applied to methods like ion-exchange chromatography to yield the amino acid or which is then made acidic and extracted with an organic solvent such as diethylether and toluene to remove an organic layer, and then an aqueous layer is made basic and extracted similarly with an organic solvent to remove an aqueous layer, and then the solvent is evaporated off under reduced pressure, and a further purification is performed if necessary, for example, by a chromatography and the like to yield the amino acid.

Also in the present invention the optical purity of the amino acid (1) may be increased by reacting the biological material of the present invention with said amino acid.

Such method may be performed in the conditions similar to various conditions relevant to the method of the present invention described above.

A longer reaction time generally results in a higher optical purity of the amino acid (1) obtained due to an increase in the conversion rate. By subjecting the amino acid (1) which are remaining in the reaction mixture still after the reaction to an appropriate combination of known methods, the amino acid (1) in which the rate of one optical isomer is higher than that before the reaction may readily be recovered.

EXAMPLES

The present invention is further detailed in the following examples which are not intended to restrict the present invention.

Example 1

A 500 mL Sakaguchi flask containing 100 ml of a sterilized medium (pH 7.0) containing 1.0% (w/v) glycerol, 0.2% (w/v) polypeptone (Nihon Pharmaceutical Co., Ltd.), 0.3% (w/v) meat extract powder (Kyokuto Pharmaceutical Ind., Co., Ltd.), 0.3% (w/v) yeast extract (Difco), 0.1% (w/v) dipotassium phosphate, 0.1% (w/v) mono potassium phosphate, 0.03% (w/v) magnesium sulfate heptahydrate was inoculated with 1 mL of a culture of *Nocardia diaphanozonaria* strain JCM3208 which had previously been cultivated in a medium of the similar composition, and incubated at 30° C. for 3 days with a reciprocal shaking. From this culture, cells were collected by centrifugation (10000 g, 10 minutes), which was combined with 10 ml of 100 mM potassium phosphate buffer (pH 7.0) to form a cell suspension again, which was centrifuged (10000 g, 10 minutes) to obtain wet cells. The wet cells thus obtained were suspended in 10 mL of 100 mM potassium phosphate buffer (pH 7.0) to obtain a cell suspension 50 mg of D-p-chlorophenylalamine was dissolved in 45 mL of an aqueous solution (pH 7.0) containing 0.15% (w/v) mono potassium dihydrogen phosphate, 0.15% (w/v) disodium hydrogen mono phosphate, 0.02% (w/v) magnesium sulfate heptahydrate, 0.001% (w/v) ferrous sulfate heptahydrate, 0.001% (w/v) zinc sulfate heptahydrate, 0.001% (w/v) manganese sulfate trihydrate, 0.001% cobalt chloride hexahydrate and 0.0005% (w/v) yeast extract, to which 5 ml of the cell suspension described above was added and the reaction mixture was kept at 30° C. for 74 hours with stirring using a magnetic stirrer at 1000 rpm. Subsequently, an aliquot of the reaction mixture was taken and centrifuged to remove the cell and the supernatant obtained was subjected to HPLC to ensure that L-p-chlorophenylalanine at the optical purity of 100% e.e. was obtained at 79 yield.

Example 2

The reaction was performed by the procedure similar to that in Example 1 except for using a racemic p-chlorophenylalanine instead of D-p-chlorophenylalanine and reaction time of 24 hours instead of reaction time of 74 hours. Subsequently, an aliquot of the reaction mixture was taken and centrifuged to remove the cell and the supernatant obtained was subjected to HPLC to ensure that L-p-chlorophenylalanine at the optical purity of 72% e.e. was obtained at 82% yield.

On the other hand, the reaction was performed by the procedure similar to that in Example 1 except for using L-p-chlorophenylalanine instead of D-p-chlorophenylalanine. Subsequently, an aliquot of the reaction mixture was taken and centrifuged to remove the cell and the supernatant obtained was subjected to HPLC for an analysis of products, which revealed no formation of D-p-chlorophenylalanine.

Example 3

A 10 mL test tube containing 3 ml of a sterilized medium (pH 7.0) containing 1.0% (w/v) glycerol, 0.2% (w/v) polypeptone (Nihon Pharmaceutical Co., Ltd.), 0.3% (w/v) meat extract powder (Kyokuto Pharmaceutical Ind., Co., Ltd.), 0.3% (w/v) yeast extract (Difco), 0.1% (w/v) dipotassium phosphate, 0.1% (w/v) mono potassium phosphate, 0.03% (w/v) magnesium sulfate heptahydrate was inoculated with a "loopful" of a culture of each microorganism shown in Table I which had previously been frozen in a 30% (w/v) aqueous solution of glycerol at −80° C., and incubated at 30° C. for 2 days with a reciprocal shaking. From this culture, cells were collected by centrifugation (10000 g, 10 minutes), which were combined with 3 ml of 100 mM potassium phosphate buffer (pH 7.0) to form a cell suspension again, which was centrifuged (10000 g, 10 minutes) to obtain wet cells. This was combined with 3 mL of an aqueous solution (pH7.0) containing 0.1% (w/v) D-p-chlorophenylalanine, 0.15% (w/v) mono potassium dihydrogen phosphate, 0.15% (w/v) disodium mono hydrogen phosphate, 0.02% (w/v) magnesium sulfate heptahydrate, 0.001% (w/v) ferrous sulfate heptahydrate, 0.001% (w/v) zinc sulfate heptahydrate, 0.001% (w/v) manganese sulfate trihydrate, 0.001% (w/v) cobalt chloride hexahydrate and 0.0005% (w/v) yeast extract and the culture was kept at 30° C. for a time period shown in Table 1 with a reciprocal shaking at 250 rpm. The results are shown in Table 1.

TABLE 1

| Biological material | Incubation time (h) | % L-form | % D-form |
|---|---|---|---|
| Arthrobacter pascens strain IFO12139 | 72 | 64 | 36 |
| Flavimonas oryzihabitans strain JCM2952 | 72 | 90 | 10 |
| Klebsiella planticola strain JCM7251 | 48 | 61 | 39 |
| Pseudomonas chlororaphis strain IFO3521 | 72 | 94 | 6 |
| Pseudomonas oleovorans strain IFO13583 | 48 | 89 | 11 |
| Pseudomonas oxalaticus strain IFO13593 | 48 | 75 | 25 |
| Pseudomonas taetrolens strain IFO3460 | 72 | 90 | 10 |
| Rhizobium meliloti strain IFO14782 | 48 | 84 | 16 |

TABLE 1-continued

| Biological material | Incubation time (h) | % L-form | % D-form |
|---|---|---|---|
| Saccharopolyspora hirsuta subsp. kobensis strain JCM9109 | 72 | 67 | 33 |
| Streptomyces roseus strain IFO12818 | 48 | 96 | 4 |

On the other hand, the test described above was performed similarly except for using L-p-chlorophenylalanine instead of D-p-chlorophenylalanine. The results are shown in Table 2.

TABLE 2

| Biological material | Incubation time (h) | % L-form | % D-form |
|---|---|---|---|
| Arthrobacter pascens strain IFO12139 | 72 | 100 | 0 |
| Flavimonas oryzihabitans strain JCM2952 | 72 | 100 | 0 |
| Klebsiella planticola strain JCM7251 | 48 | 100 | 0 |
| Pseudomonas chlororaphis strain IFO3521 | 72 | 100 | 0 |
| Pseudomonas oleovorans strain IFO13583 | 48 | 100 | 0 |
| Pseudomonas oxalaticus strain IFO13593 | 48 | 100 | 0 |
| Pseudomonas taetrolens strain IFO3460 | 72 | 100 | 0 |
| Rhizobium meliloti strain IFO14782 | 48 | 100 | 0 |
| Saccharopolyspora hirsuta subsp. kobensis strain JCM9109 | 72 | 100 | 0 |
| Streptomyces roseus strain IFO12818 | 48 | 100 | 0 |

Example 4

10 mg of each amino acid, shown in Table 3, which is a racemic mixture was dissolved in 9 ml of an aqueous solution (pH7.0) containing 0.15% (w/v) mono potassium dihydrogen phosphate, 0.15% (w/v) disodium mono hydrogen phosphate, 0.02% (w/v) magnesium sulfate heptahydrate, 0.001% (w/v) ferrous sulfate heptahydrate, 0.001% (w/v) zinc sulfate heptahydrate, 0.001% (w/v) manganese sulfate trihydrate, 0.001% cobalt chloride hexahydrate and 0.0005% (w/v) yeast extract. 2.7 mL of the aqueous solution containing the respective amino acid as a racemic mixture was combined with 0.3 ml of a cell suspension prepared similarly as in Example 1 and incubated at 30° C. for the respective time period shown in Table 3 with a reciprocal shaking at 250 rpm. The results are shown in Table 3.

TABLE 3

| Substrate amino acid (racemic mixture) | Incubation time (h) | % L-form | % D-form |
|---|---|---|---|
| Norvaline | 48 | 96 | 4 |
| phenylglycine | 48 | 100 | 0 |
| methionine | 72 | 69 | 31 |
| 2-aminobutyric acid | 72 | 70 | 30 |

Example 5

10 mg of each amino acid, shown in Table 4, which is a D-form was dissolved in 9 ml of an aqueous solution (pH7.0) containing 0.15% (w/v) mono potassium dihydrogen phosphate, 0.15% (w/v) disodium mono hydrogen phosphate, 0.02% (w/v) magnesium sulfate heptahydrate, 0.001% (w/v) ferrous sulfate heptahydrate, 0.001% (w/v) zinc sulfate heptahydrate, 0.001% (w/v) manganese sulfate trihydrate, 0.001% (w/v) cobalt chloride hexahydrate and 0.0005% (w/v) yeast extract. 2.7 mL of the aqueous solution containing the respective amino acid as a D-form was combined with 0.3 ml of a cell suspension prepared similarly as in Example 1 and incubated at 30° C. for the respective time period shown in Table 4 with a reciprocal shaking at 250 rpm. The results are shown in Table 4.

TABLE 4

| Substrate amino acid (D-form) | Incubation time (h) | % L-form | % D-form |
|---|---|---|---|
| Norvaline | 48 | 99 | 1 |
| Phenylglycine | 70 | 98 | 2 |
| Methionine | 70 | 39 | 61 |
| tert-Leucine | 47 | 7 | 93 |
| 2-Aminobutyric acid | 70 | 62 | 38 |
| Naphthylalanine | 96 | 56 | 44 |

On the other hand, the test described above was performed similarly except for using the respective L-amino acid instead of each D-amino acid. The results are shown in Table 5.

TABLE 5

| Substrate amino acid (L-form) | Incubation time (h) | % L-form | % D-form |
|---|---|---|---|
| Norvaline | 72 | 100 | 0 |
| Phenylglycine | 72 | 100 | 0 |
| Methionine | 48 | 100 | 0 |
| tert-Leucine | 72 | 100 | 0 |
| α-Aminobutyric acid | 48 | 100 | 0 |
| Naphthylalanine | 96 | 100 | 0 |

Example 6

A 500 mL Sakaguchi flask containing 100 ml of a sterilized medium (pH 7.0) containing 1.0% (w/v) glycerol, 0.2% (w/v) polypeptone (Nihon Pharmaceutical Co., Ltd.), 0.3% (w/v) meat extract (Kyokuto Pharmaceutical Ind., Co., Ltd.), 0.3% (w/v) yeast extract (Difco), 0.1% (w/v) dipotassium phosphate, 0.1% (w/v) potassium mono phosphate, 0.03% (w/v) magnesium sulfate heptahydrate was inoculated with 1 mL of a culture of *Nocardia diaphanozonaria* strain JCM3208 which had previously been cultivated in a medium of the similar composition, and incubated at 30° C. for 2 days with a reciprocal shaking. 80 ml of this culture was subjected to centrifugation (10000 g, 10 minutes) to collect wet cells. The collected wet cells were washed twice with 80 ml of 100 mM potassium phosphate buffer (pH 7.0) and the wet cells thus obtained was suspended in 4 mL of 100 mM potassium phosphate buffer (pH 7.0) to obtain a cell suspension.

0.2 ml of the cell suspension was combined with 1.8 mL of 100 mM potassium phosphate buffer (pH7.0) containing D-p-chlorophenylalanine at 5.5 mM and an aminotransferase inhibitor shown in Table 6 at 1.1 mM, and incubated at 30° C. for 2 hours with a reciprocal shaking at 250 rpm. Each reaction mixture was analyzed at an early stage of the reaction by HPLC to quantify L-p-chlorophenylalanine produced by the reaction. The results are represented as the relative values each based on 100% production of L-p-chlorophenylalanine in the absence of the respective aminotransferase inhibitor.

TABLE 6

| Amino acid transferase inhibitor (final concentration 1 mM) | Relative value (%) |
|---|---|
| Absence | 100 |
| β-Chloro-D-alanine | 108 |
| β-Chloro-L-alanine | 121 |
| DL-Gabaculine | 92 |

Example 7

The reaction was performed similarly as in Example 6 except for using each of the microorganisms shown in Table 7 instead of *Nocardia diaphanozonaria* strain JCM3208. The results are shown in Table 7.

TABLE 7

| | Relative value (%) | | | |
|---|---|---|---|---|
| Biological material | Absence | β-Chloro-D-alanine | β-Chloro-L-alanine | Gabaculine |
| *Flavimonas oryzihabitans* JCM2952 | 100 | 144 | 92 | 105 |
| *Klebsiella planticola* JCM7251 | 100 | 90 | 92 | 102 |
| *Pseudomonas chlororaphis* IFO3521 | 100 | 85 | 102 | 72 |
| *Pseudomonas oleovorans* IFO13583 | 100 | 91 | 94 | 87 |
| *Pseudomonas taetrolens* IFO3460 | 100 | 84 | 87 | 75 |
| *Rhizobium meliloti* IFO14782 | 100 | 108 | 96 | 88 |

Example 8

The reaction was performed similarly as in Example 6 except for using each of the microorganisms shown in Table 8 instead of *Nocardia diaphanozonaria* strain JCM3208 and except that the reaction time was 24 hours (when the reaction was equilibrated). The results are shown in Table 8.

TABLE 8

| | Relative value (%) | | | |
|---|---|---|---|---|
| Biological material | Absence | P-Chloro-D-alanine | P-Chloro-L-alanine | Gabaculine |
| *Arthrobacter pascens* IFO12139 | 100 | 83 | 84 | 96 |
| *Pseudomonas oxalaticus* IFO13593 | 100 | 124 | 91 | 105 |
| *Saccharopolyspora hirsuta* JCM9109 | 100 | 99 | 101 | 97 |
| *Streptomyces roseus* IFO12818 | 100 | 114 | 95 | 97 |

EFFECT OF THE INVENTION

According to the present invention, an optically active amino acid which is useful as an intermediate for a pharmaceutical and as a feed or food additive can efficiently be produced.

What is claimed is:

1. A method for producing from an optical isomer I of an amino acid represented by Formula (I):

$$R\text{---}CH(NH_2)\text{---}COOH \qquad (1)$$

wherein R is an optionally substituted C1–C12 alkyl group, an optionally substituted C4–C8 cycloalkyl group or an optionally substituted C6–C14 aryl group, an optical isomer II, said method comprising reacting a biological material which has an ability of converting said optical isomer I to said optical isomer II, the isomerism being on the basis of an asymmetric carbon atom to which both of an amino group and a carboxyl group are bound and said ability being not inhibited seriously by an aminotransferase inhibitor β-chloro-D-alanine, β-chloro-L-alanine or gabaculine, with said optical isomer I, wherein said biological material is one obtained from a microorganism belonging to the genus Arthrobacter, Klebsiella, Nocardia, Rhizobium, Saccharopolyspora or Streptomyces.

2. The method according to claim 1, wherein said optical isomer I reacted with said biological material is contained in a racemic mixture of said optical isomers I and II.

3. A method for producing from an optical isomer I of an amino acid represented by Formula (I):

$$R\text{---}CH(NH_2)\text{---}COOH \qquad (1)$$

wherein R is an optionally substituted C1–C12 alkyl group, an optionally substituted C4–C8 cycloalkyl group or an optionally substituted C6–C14 aryl group, an optical isomer II, said method comprising reacting a biological material which has an ability of converting said optical isomer I to said optical isomer II, the isomerism being on the basis of an asymmetric carbon atom to which both of an amino group and a carboxyl group are bound and said ability being not inhibited seriously by an aminotransferase inhibitor β-chloro-D-alanine, β-chloro-L-alanine or gabaculine, with said optical isomer I, wherein said biological material is one obtained from a microorganism classified to *Arthrobacter pascens, Flavimonas oryzihabitans, Klebsiella planticola, Nocardia diaphanozonaria, Pseudomonas chlororaphis, Pseudomonas oleovorans, Pseudomonas oxalaticus, Pseudomonas taetrolens, Rhizobium meliloti, Saccharopolyspora hirsuta* or *Streptomyces roseus.*

4. A method for producing from an optical isomer I of an amino acid represented by Formula (I):

$$R\text{---}CH(NH_2)\text{---}COOH \qquad (1)$$

wherein R is an optionally substituted C1–C12 alkyl group, an optionally substituted C4–C8 cycloalkyl group or an optionally substituted C6–C14 aryl group, an optical isomer II, said method comprising reacting a biological material which has an ability of converting said optical isomer I to said optical isomer II, the isomerism being on the basis of an asymmetric carbon atom to which both of an amino group and a carboxyl group are bound and said ability being not inhibited seriously by an aminotransferase inhibitor β-chloro-D-alanine, β-chloro-L-alanine or gabaculine, with said optical isomer I, wherein said biological material is one obtained from *Arthrobacter pascens* strain IFO12139, *Flavimonas oryzihabitans* strain JCM2952, *Klebsiella planticola* strain JCM7251, *Nocardia diaphanozonaria* strain JCM3208, *Pseudomonas chlororaphis* strain IFO3521, *Pseudomonas oleovorans* strain IFO13583, *Pseudomonas oxalaticus* strain IFO13593, *Pseudomonas taetrolens* strain IFO3460, *Rhizobium meliloti* strain IFO14782, *Saccharopolyspora hirsuta* subsp. *kobensis* strain JCM9109 or *Streptomyces roseus* strain IFO12818.

5. The method according to claim 1, 3 or 4, wherein said optical isomer I is a D-form and said optical isomer II is a L-form.

6. The method according to claim 1, 3 or 4, wherein said optical isomer I with which said biological material is reacted is present in a mixture with optical isomer II.

7. The method according to claim 1, 3 or 4, wherein said biological material is a whole cell.

8. A method for producing from an optical isomer I of an amino acid represented by Formula (I):

$$R\text{---}CH(NH_2)\text{---}COOH \qquad (1)$$

wherein R is an optionally substituted C1–C12 alkyl group, an optionally substituted C4–C8 cycloalkyl group or an optionally substituted C6–C14 aryl group, said method comprising reacting a biological material which has an ability of converting an optical isomer I of said amino acid to an optical isomer II, the isomerism being on the basis of an asymmetric carbon atom to which both of an amino group and a carboxyl group are bound and said ability being not inhibited seriously by an aminotransferase inhibitor β-chloro-D-alanine, β-chloro-L-alanine or gabaculine, with a racemic mixture of said optical isomers I and II.

9. The method according to claim 8, wherein said optical isomer I is a D-form and said optical isomer II is a L-form.

10. The method according to claim 8, wherein said biological material is one obtained from a microorganism classified to Arthrobacter pascens, Flavimonas oryzihabitans, Klebsiella planticola, Nocardia diaphanozonaria, Pseudomonas chlororaphis, Pseudomonas oleovorans, Pseudomonas oxalaticus, Pseudomonas taetrolens, Rhizobium meliloti, Saccharopolyspora hirsutaor *Streptomyces roseus.*

11. The method according to claim 8, wherein said biological material is one obtained from *Arthrobacter pascens* strain IFO12139, *Flavimonas oryzihabitans* strain JCM2952, *Klebsiella planticola* strain JCM7251, *Nocardia diaphanozonaria* strain JCM3208, *Pseudomonas chlororaphis* strain IFO3521, *Pseudomonas oleovorans* strain IFO13583, *Pseudomonas oxalaticus* strain IFO13593, *Pseudomonas taetrolens* strain IFO3460, *Rhizobium meliloti* strain IFO14782, *Saccharopolyspora hirsuta* subsp.*kobensis* strain JCM9109 or *Streptomyces roseus* strain IFO12818.

* * * * *